United States Patent [19]

Matsuo

[11] 4,267,828

[45] May 19, 1981

[54] ENDOSCOPE HAVING AN EXTENSION GUIDE FOR OBSERVATION

[75] Inventor: Kazumasa Matsuo, Hachioji, Japan

[73] Assignee: Olympus Optical Co., Ltd., Tokyo, Japan

[21] Appl. No.: 51,032

[22] Filed: Jun. 22, 1979

[51] Int. Cl.³ .............................................. A61B 1/06
[52] U.S. Cl. ....................................... 128/6; 350/96.26
[58] Field of Search ........................................ 128/3–8; 356/241; 350/96.25, 96.26; 138/131, 134, 118, 139

[56] References Cited

U.S. PATENT DOCUMENTS

| 207,489 | 8/1878 | Bourguignon | 138/131 |
|---|---|---|---|
| 2,975,785 | 3/1961 | Sheldon | 128/6 |
| 3,690,775 | 9/1972 | Cousins | 356/241 |
| 3,699,950 | 10/1972 | Humphrey, Jr. et al. | 350/96.26 |
| 3,778,170 | 12/1973 | Howell et al. | 356/241 |
| 3,822,697 | 7/1974 | Komiya | 128/3 |

FOREIGN PATENT DOCUMENTS

| 2405054 | 6/1979 | France | 128/6 |
|---|---|---|---|
| 282136 | 9/1961 | Netherlands | 128/6 |

Primary Examiner—Robert W. Michell
Assistant Examiner—Arthur S. Rose

[57] ABSTRACT

A flexible, tubular extension guide has its one open end fixed to a control section housing constituting a grip or operation section of an endoscope and its external free end connected to an eyepiece section of an observation system. The guide can be bent in any direction such that the eyepiece section can be set in any desired position, and self-retained at that bent position. The base end portion of an optical fiber bundle of an observation system is introduced into the guide and the base end of the bundle is directly optically connected to the eyepiece section.

2 Claims, 3 Drawing Figures

ENDOSCOPE HAVING AN EXTENSION GUIDE FOR OBSERVATION

BACKGROUND OF THE INVENTION

This invention relates to an endoscope having an extension guide for observation.

In an endoscope of this type an extension guide is a stub shaft-like section fixed slantwise, for example, at the side wall of a control section housing where an operator operates the endoscope, and an eyepiece section for observation is fitted to the free end portion of the guide. Such a construction is often found in an endoscope of such a type that the base end of a channel tube having a channel for inserting a body cavity treating instrument such as a catheter therein extends through that end wall of the housing which is provided on the side opposite to that in which a sheath to be introduced into the body cavity of a human being is connected. This is because no space enough to fix an eyepiece section is often left at that end of the housing from the standpoint of design consideration. A prism is disposed between the eyepiece section on the extension guide and the base end of an optical fiber bundle which extends from the sheath into the housing. The base end of the optical fiber bundle is optically connected the eyepiece by bending an optical axis through the utilization of the prism. In such a structure a higher degree of skill is required in the adjustment of an observation optical system and, by doing so, the misalignment problem is liable to occur. Further, as the extension guide is limited in its length the operator requires some effects during the observation through the eyepiece section. This is partly due to the fact that as the extension guide is rigid the angle and position of the eyepiece section are restricted. Thus, a cumbersome manual operation is required at the control section housing so that ROI (region of interest) within the body cavity can be observed. Since the eyepiece section is so restricted, such inconvenience is added.

The above-mentioned problem is involved in the endoscope having an eyepiece section not only at the side of the housing, but also at the end of the housing.

SUMMARY OF THE INVENTION

It is accordingly the object of this invention to provide an endoscope free from the above-mentioned drawbacks, which can obtain an accurate optical system without requiring any particular adjustment of an observation system at the manufacture and assembly stage.

According to this invention, an extension guide is flexible and is bent and self-retained such that an eyepiece section can be set in a desired position. The guide has its end opened in a control section housing through which the base end portion of an optical fiber bundle is introduced into the extension guide such that the base end of the bundle is optically connected to the eyepiece section. Since the extension guide is flexible in nature the operator can set the extension guide at a desired angle or position so that good observation can be obtained. The fiber bundle portion per se which is introduced into the guide is flexible and thus the flexibility of the guide is not impaired. At the assembly stage, no particular adjustment of the optical system is required because no prism is interposed between the base end of the fiber bundle and the eyepiece section.

BRIEF DESCRIPTION OF THE DRAWINGS

This invention will be further described by way of example by referring to the accompanying drawings in which.

DESCRIPTION OF THE PREFERRED EMBODIMENTS

Figure 1:
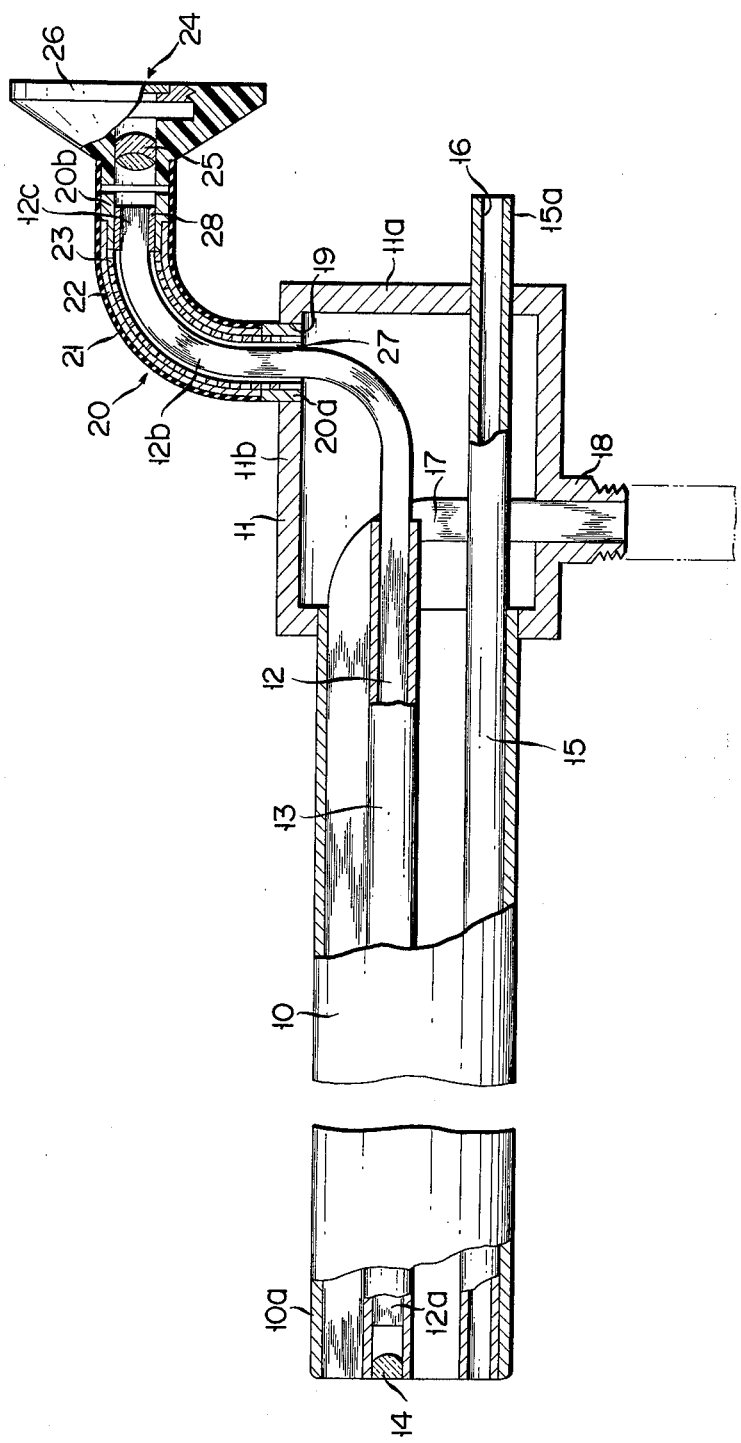
FIG. 1 is a partial, longitudinal cross-section showing an endoscope according to one embodiment of this invention.

An endoscope as shown in FIG. 1 is what is called laparoscope having a straight rigid sheath 10. The base end portion (a right end portion in FIG. 1) of the sheath is attached to the left end of a cylindrical control section housing 11. The distal end portion 10a of the sheath 10 is inserted into the body cavity of a human being (patient). The manual operation of the sheath, as well as the observation of the body cavity, is effected at the control section. An optical fiber bundle 12 of an observation system is inserted in the sheath 10 along the length of the sheath 10. An optical fiber bundle is inserted into a straight metal guide pipe 13 which is in turn inserted into the sheath 10. The pipe 13 is (held) by a proper means (not shown) within the sheath 10. The distal end 12a of the bundle is optically connected to a lens 14 which is exposed to the outside of the sheath 10. A channel tube 15 is disposed with the sheath 10 parallel to the bundle 12 such that it is held in place by a proper means (not shown), and extends into the housing. The distal end of the channel tube 15 is opened at the distal end 10a of the sheath and the base end 15a of the channel tube extends through that housing end 11a remote from the sheath 10. An insertion instrument (not shown) such as a catheter is inserted into a channel 16 of the tube 15 from the base end side of the tube 15. A light conducting fiber bundle 17 for illumination is disposed within the sheath 10. The base end of the bundle 17 extends up to a connector 18 provided on the housing 11. The connector 18 is connected to an external light source, not shown, by a code as indicated by dot-dash lines. A hole 19 is provided in the cylindrical side wall 11b of the housing 11, and one end 20a of a tubular extension guide 20 is rigidly fixed at the hole 19 in the side wall of the housing 11. The guide 20 is formed of three layers 21, 22, 23. An eyepiece section 24 is fitted into an outer, free end portion 20b of the guide 20. The eyepiece section 24 includes an eyepiece 25 and lens cover 26, but the structure of the eyepiece section 24 is known in the art.

The innermost layer 23 of the extension guide 20 is formed of a helical wire and serves to give reinforced flexibility to the guide. The intermediate layer 22 is formed of a synthetic resin tube or a thin-walled metal tube made of copper, tin, lead etc. which is malleable and self-retainable in the bent state. The outermost layer 21 is made of a soft tube made of synthetic resin or rubber. The three-layers are intimately united together to permit the extension guide 20 to be self-retained in the bent position. The base end portion 12b of the optical fiber bundle 12 extends through a hole 27 into the guide 20 such that the base end 12c of the bundle is fixed by a set ring 28 which is attached in the guide end in a position near to the eyepiece 25 in the eyepiece section 24. In consequence, the optical fiber bundle 12 is optically connected directly to the lens 25 without interposing a prism therebetween. The base end portion 12b of the fiber bundle 12 is flexible except for its mounting end portion 12c and thus the flexibility of the guide 20 is not impeded. The bundle 12 per se has a self recoverable elasticity, but the guide 20 can be self retained in any bent position against the elastic recovery of the bundle 12.

Figure 2:
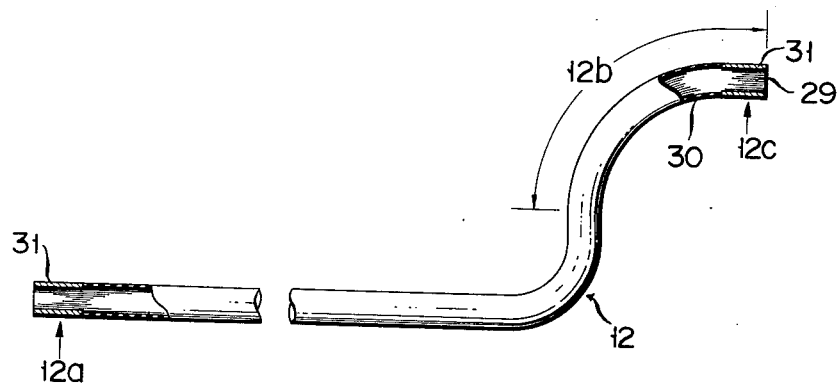
FIG. 2 shows a detail of an optical fiber bundle of the endoscope of FIG. 1.
Figure 3:
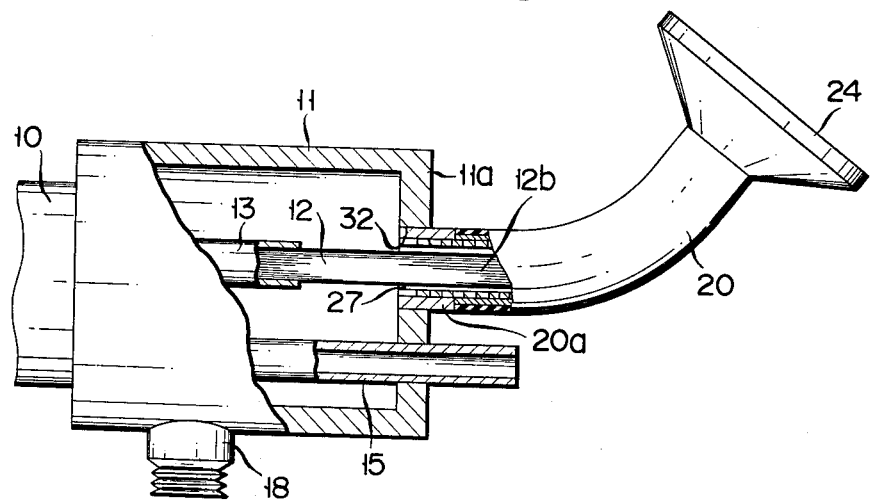
FIG. 3 is a partial, longitudinal cross-section showing an endoscope according to another embodiment of this invention in which an extension guide is provided at the end of a control section housing.

The fiber bundle 12 as shown in FIGS. 1 and 3 is shown in detail in FIG. 2. The bundle 12 is constituted of a bundle of thin glass fibers 29 and the outer surface of the bundle is covered with a very thin tube 30, though in FIGS. 1 and 3 the fibers of the bundle are shown in the exposed state. A ring-like clamp 31 is fitted over the distal end portion 12a and over the mounting base end portion 12c of the bundle 12. These end portions are rigidly united together and both the ends of the bundle 12 are polished flat. In FIGS. 1 and 3 the clamp is not shown for brevity.

A variety of fiber bundle manufacturing methods have been proposed up to this date. In this embodiment the following method is used. That is, the fiber bundle 12 is formed by bundling together optical fibers 29, covering them with glass material, for example, an acid-soluble glass and drawing it under heating to provide a glass rod-like conduit. In this case, the flexible portion of the fiber bundle is formed by dipping a desired fiber bundle portion in, for example, nitric acid to dissolve the coated glass material. The distal end portion 12a and mounting base end portion 12c of the fiber bundle 12 have their covered glass material left unsolved with the acid.

That fiber bundle portion inserted in the extension guide 20, i.e. the base end portion 12b of the fiber bundle (see FIG. 2), except for its mounting end portion 12c should be left as the flexible portion. This fiber bundle portion has its covered glass material solved with the acid. The remaining fiber bundle portion can be left covered with the glass material. By so doing the breakage of the fibers of the bundle 12 is decreased to a maximum possible extent, improving the drability of the fiber bundle. Therefore, the covered length of the fiber bundle is not restricted to the distal end portion 12a and mounting base end portion 12c.

FIG. 3 shows an endoscope according to another embodiment of this invention. In this embodiment an extension guide is fixed at the end 11a of a control section housing 11. Generally, a channel tube 15 extends through the end 11a of the housing and a narrow space is left at the end 11a of the housing. If there is an ample space at the end 11a of the housing the embodiment as shown in FIG. 2 can be adopted. In the embodiment as shown in FIG. 2 an extension guide is exactly the same as that of FIG. 1 and the other arrangement is the same except for the following points. The same reference numerals are used in FIG. 2 to denote parts or elements corresponding to those shown in FIG. 1. That is, a guide mounting hole 32 is provided at the end 11a of the housing 11, a guide pipe 13 for a fiber bundle 12 extends a little right within the housing, and the fiber bundle 12 extends from the base end of the pipe 13 straight toward an opening 27 in the end 20a of the extension guide.

In the embodiment of FIG. 3 an eyepiece section 24 fixed into the free end portion of the guide 20 can be bent in a position as shown in FIG. 3 or in the other direction, because the extension guide 24 is flexible in nature. If, for example, the eyepiece section occupies the position as shown in FIG. 3, it will provide no obstacle to the insertion of an insertion instrument such as a catheter into a tube 15.

In the embodiment as shown in FIGS. 1 and 3 the extension guide can be bent in any desired direction, as required, so that the eyepiece section can be set in a desired position. Since the fiber bundle can be extended directly up to the eyepiece section, the extension guide per se can be designed to have an enough length and thus an observation operation can be easily made. As a result, the operator can observe ROI in the body cavity over a longer time without fatigue.

Since a prism is not used in the optical system, no cumbersome adjustment of the optical system is necessary and thus no misalignment problem arises therefrom.

What is claimed is:

1. An endoscope comprising:
    an elongated rigid sheath to be introduced in the body cavity, said sheath having a distal end and a base end,
    a control section housing having a side wall and a pair of end walls, said base end of the sheath being attached to one of the end walls,
    an extension guide having an open end fixed to the control section housing to communicate with the interior of the housing and an outer free end into which an eyepiece is fitted, said guide being flexible along its length such that it may be bent into a plurality of angular orientations with respect to said housing, and
    a single optical fiber bundle of an observation system made of many thin glass fibers and having a distal end inserted within the sheath and a base end portion extended into the extension guide through said housing and said open end of the extension guide, said base end portion of the fiber bundle having a mounting base end fixed to the extension guide in a position near to the eyepiece and directly optically connected to the eyepiece without interposing a prism therebetween,
    said base end portion of said fiber bundle having a flexibility except for the mounting base end and the glass fibers of the remaining portion of the fiber bundle being united together in a rigid glass rod-like fashion.

2. An endoscope according to claim 1, further comprising a rigid and straight channel tube for an insertion instrument such as a catheter, said channel tube having a distal end opened at the distal end of the sheath and a base end outwardly extended through the other end wall of the control section housing, in which said open end of the extension guide is fixed in the side wall of the control section housing.

* * * * *